US006403371B1

(12) United States Patent
Conrad et al.

(10) Patent No.: US 6,403,371 B1
(45) Date of Patent: Jun. 11, 2002

(54) CASSETTES FOR THE EXPRESSION OF STORABLE PROTEINS IN PLANTS

(75) Inventors: Udo Conrad, Hausneindorf; Ulrike Fielder, Gatersleben; Julian Phillips, Gatersleben; Olga Artsaenko, Gatersloben, all of (DE)

(73) Assignee: Institut für Pflanzengenetik und Kulturpflanzenforschung (DE)

( * ) Notice: Subject to any disclaimer, the term of this patent is extended or adjusted under 35 U.S.C. 154(b) by 0 days.

(21) Appl. No.: 09/117,990

(22) PCT Filed: Feb. 7, 1997

(86) PCT No.: PCT/DE97/00285

§ 371 (c)(1),
(2), (4) Date: Dec. 7, 1998

(87) PCT Pub. No.: WO97/29200

PCT Pub. Date: Aug. 14, 1997

(30) Foreign Application Priority Data

Feb. 8, 1996 (DE) ......................................... 196 04 588
May 23, 1996 (DE) ......................................... 196 20 804

(51) Int. Cl.$^7$ ......................... C12N 15/29; C12N 15/13; C12N 15/82; C12N 15/62; C07H 21/02
(52) U.S. Cl. .................. 435/320.1; 536/23.1; 536/24.1; 536/23.4; 435/69.8; 800/287; 800/288
(58) Field of Search ................................ 536/24.1, 23.1, 536/23.4; 800/287, 288; 435/468, 471, 41, 418, 419, 320.1, 69.8

(56) References Cited

FOREIGN PATENT DOCUMENTS

| DE | 263031 | 12/1988 |
| DE | 275479 | 1/1990 |

OTHER PUBLICATIONS

Kim et al. Plant Molecular Biology. 1994. vol. 24: 105–117.*
Baumlein et al. Molecular and General Genetics. 1991. 225: 459–467.*
Haq et al. Science. 1995. vol. 268: 714–716.*
Baumlein et al. Molecular and General Genetics. 1991. 225: 121–128.*
Tavladoeaki et al. Nature. 1993. vol. 366: 469–472.*
O.Artsaenko et al.; Expression of a Single–chain Fv Antibody Against Abscisic Acids Creates a Wilty Phenotype in Transgenic Tobacco; The Plant Journal (1995) 8(5), pp. 745–750.
U. Fiedler et al; High–Level Production and Long–term Storage of Engineered Antibodies in Transgenic Tobacco Seeds; Biotechnology vol. 13 Oct. 1995; pp. 1090–1093.
C. Wandelt et al.; Vicilin with Carboxy–terminal KDEL is Retained in the Endoplasmic Reticulum and Accumulates to High Levels in the Leaves of Transgenic Plants; The Plant Journal (1992) 2 (2), pp. 181–192.
U. Conrad et al.; Expression of Engineered Antibodies in Plant Cells; Plant Molecular Biology 26; 1994; pp. 1023–1030.
S. Firek et al.; Secretion of a Functional Single–chain Fv Protein in Transgenic Tobacco Plants and Cell Suspension Cultures; Plant Molecular Biology 23: 1993 pp. 861–870.

* cited by examiner

*Primary Examiner*—David T. Fox
*Assistant Examiner*—Ousama Zaghmout
(74) *Attorney, Agent, or Firm*—Norris, McLaughlin & Marcus P.A.

(57) ABSTRACT

The invention relates to cassettes for the expression of storable gene products in leaves and specifically in seeds, especially single-chain antibody fragments in leaves and seeds of transgenic tobacco and pea plants. The fields of application of the invention are biotechnology, medicine (diagnosis and therapy), foodstuffs and plant control and agriculture. The expression cassette of the invention comprises constitutive or seed-specific promoters, the LeB4 signal peptide, a gene to be expressed and an ER retention signal. Preference is given to an expression cassette containing the CaMV 35S promoter as the constitutive promoter, the gene for a single-chain antibody fragment as the gene and the amino acid sequence KDEL as the ER retention signal.

4 Claims, 8 Drawing Sheets

CASSETTES FOR THE EXPRESSION OF STORABLE PROTEINS IN PLANTS

TITLE OF THE INVENTION

BACKGROUND OF THE INVENTION

The invention relates to cassettes for the expression of storable proteins in plants, especially of single-chain antibody fragments in transgenic tobacco or pea plants.

Areas of application of the invention are biotechnology, medicine (diagnostics and therapy), food and plant monitoring, as well as agriculture.

Established and reliable methods of gene cloning and gene technology and the newest developments in the technology of transgenic plants make possible further advances in plant biotechnology. Plant parts can more and more serve as production sites for materials, which are otherwise difficult to obtain. Thus, immunoglobulin has been expressed successfully in the leaves of transgenic tobacco plants. The results obtained there lie between 0.1 and 1.3% of the entire soluble protein of the leaf. The expression was either cytoplasmatic or took place in apoplasts of plant cells.

By attaching a signal for retention in the endoplasmic reticulum (ER) to a single-chain antibody gene (scFv-Gen), the antibody can be fixed in this special compartment by leaf cells of transgenic plants. This fixation leads to an increase in the expression rate of single-chain antibody fragments in leaves of transgenic plants to 4.8% of the total soluble protein (Artssenko et al., Plant J. 8, 745–750 (1995)). These findings were confirmed by others in principle, although the absolute expression values were not attained.

Further work relates to the specific expression of gene production in plant storage organs, especially in seeds. With the aid of a seed-specific promoter, single-chain antibody fragments could be expressed in a stable manner up to 0.67% of the total soluble seed protein in the seeds of transgenic tobacco plants (Fiedler and Conrad, Bio/Technology 10, 1090–1094 (1995)).

In spite of this progress, the expression rates achieved in plants were previously too low to base a plant biotechnological production of the desired materials on them.

SUMMARY OF THE INVENTION

It was therefore an object of the invention to place the seed-specific expression in transgenic plants on a basis suitable for material production. It was a further objective to achieve a biological basis for the use of a simple and manageable harvesting and processing technology, above all to assure that the gene product formed in the plant is preserved in a stable manner during the time between the direct harvest and the following extraction and purification steps in quantity and desired activity at ambient temperatures, without refrigeration.

The inventive expression cassettes contain a promoter (preferably a constitutive promoter such as the CaMV 35S promoter or a seed-specific promoter), the LeB4 signal peptide, the gene to be expressed and an ER retention signal.

BRIEF DESCRIPTION OF THE DRAWINGS

FIG. 8A represents the antigen-binding activity of purified scFv protein from fresh leaves (1), lyophilized leaves (2) and dried leaves.

DESCRIPTION OF THE PREFERRED EMBODIMENTS

Figure 1:
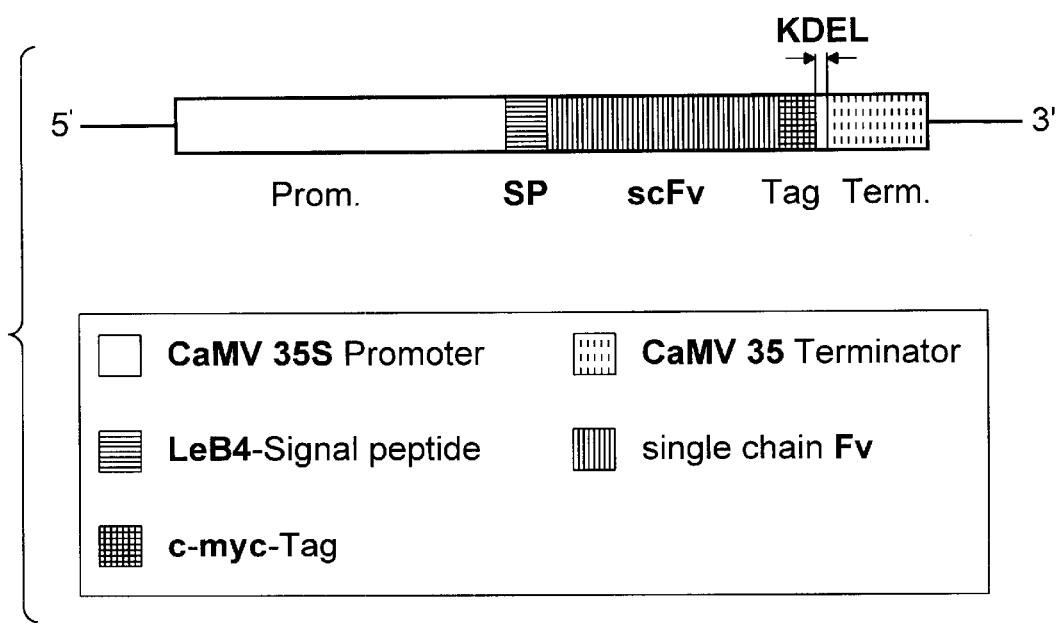
FIG. 1: Schematic representation of the cassette for the storable expression of the scFv gene in leaves of transgenic tobacco plants.
Figure 2:
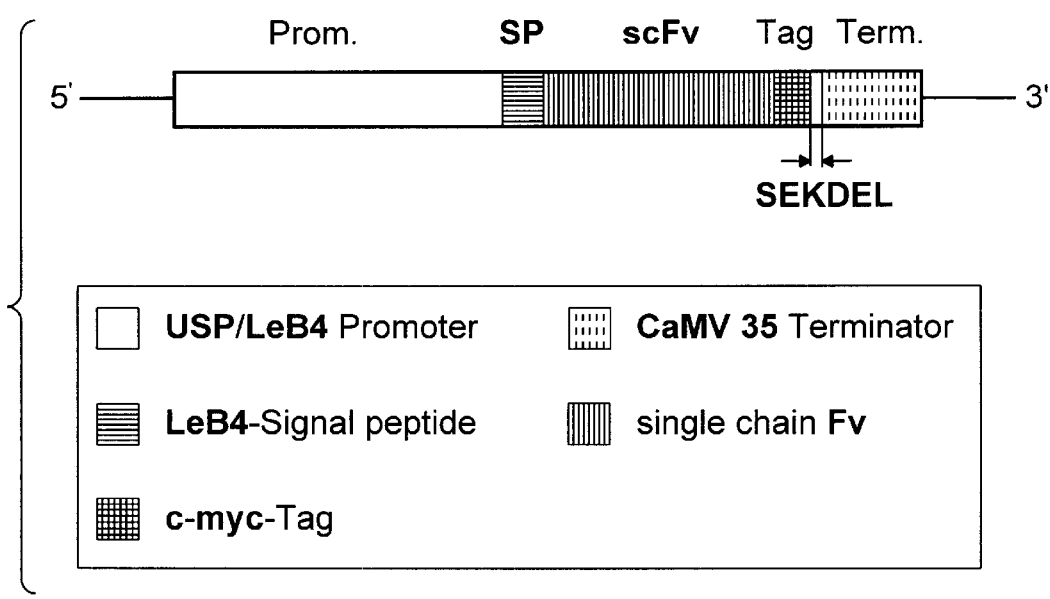
FIG. 2: Schematic representation of the cassette for seed-specific expression of the scFv gene.

The structure of the cassettes is shown schematically in FIGS. 1 and 2 on the example of a single-chain antibody gene (scFv gene).

The expression cassette of FIG. 1 is preferably used for the expression of genes of single-chain antibody fragments. It is also advantageous to use genes of recombinant antibody fragments as translation fusion with other functional proteins such as, for example, a second recombinant antibody, enzymes, toxins, chromophores and binding proteins. Preferably, the amino acid sequence KDEL (SEQ. ID no: 1) (=lysine, asparagin acid, glutamie acid, leucine) is used as the ER retention signal.

Of special importance for the inventive success of the cassette of FIG. 2 is the attachment of the specific ER retention signal SEKDEL (SEQ ID no: 2), thereby tripling or quadrupling the average expression level. Other retention signals can also be used which, occur normally in animal and vegetable proteins localized in the ER for the construction of the cassette.

In the case of the use of the LeB4 promoter, the seed-specific expression is about 1.9% of the total soluble protein, the single-chain antibody expression commencing on day 16 of the seed development. Especially advantageous is the use of the USP promoter for the construction of the expression cassette. During the seed development, it becomes active earlier, as a result of which the time period, available for concentrating the expressed product, is extended. The expression rate is therefore higher than in the case of cassettes with the LeB4 promoter.

Pursuant to the invention, the expression cassettes are transferred into bacteria strains by electroporation. The recombinant clones formed are used for the transformation of dicotyledon plants. Plants, which express gene products, are selected and grown as genetically stable lines. The gene products (among others, single-chain antibody fragments) are extracted after harvesting, possibly after drying of the plant tissue. Tobacco and pea plants are especially suitable, since they are dicotyledon plants.

The effect of the inventive cassettes was surprising, because it is known from our own electron microscopic investigations that antibodies expressed in a stable manner, for example, in the seed, are present, in ER or ER-derived vesicles even without ER retention signals. As a result, it was not to be expected that the inventive fusion would cause a clear increase in the expression level with a retention signal.

The invention makes it possible to express substances, which are otherwise difficult to obtain, such as immunoglobulin, at a high expression rate in plants, and as a result make them available for biotechnological use. Surprisingly, it has turned out that single-chain antibody fragments remain stable in storage, for example in tobacco seeds, for a long time (at least one year).

It was likewise surprising that single-chain antibody fragments expressed in leaves remain stable for several days after these leaves are dried at room temperature.

As a result, there is sufficient time for transporting from the field to the processing facilities and even for storing for some time, without loss of yield. The cause of this stability is the compartment-specific occurrence of gene products, brought about by the invention, which causes them to be protected against proteolytic breakdown.

The invention will be described in the following by some examples:

EXAMPLE 1

Expression and accumulation of the single-chain antibody fragment scFv-ox in the endoplasmic reticulum of transgenic tobacco seed.

The starting point for the experiments was a monoclonal antibody (NQ10.-12.5, Berek and Milstein, 1988 Immunol. Rev. 105, pgs. 5–26), epitopes of which are directed against an antigen which does not occur in plants (phenyloxazolone), in order to exclude possible effects on the plant metabolism. The antigen moreover has a high binding affinity. The hybridoma cell line NQ 10/12.5 is characterized by the fact that the monoclonal antibodies secreted, which are directed against the antigen, phenyloxazolone, show a high affinity (dissociation constant of $1 \times 10^8$ M) and that the specific sequences of the immunoglobulin genes are available (Berek et al., 1985). This monoclonal antibody was the point of departure for the construction of the single chain antibody fragment -scFv-ox.

Figure 3:
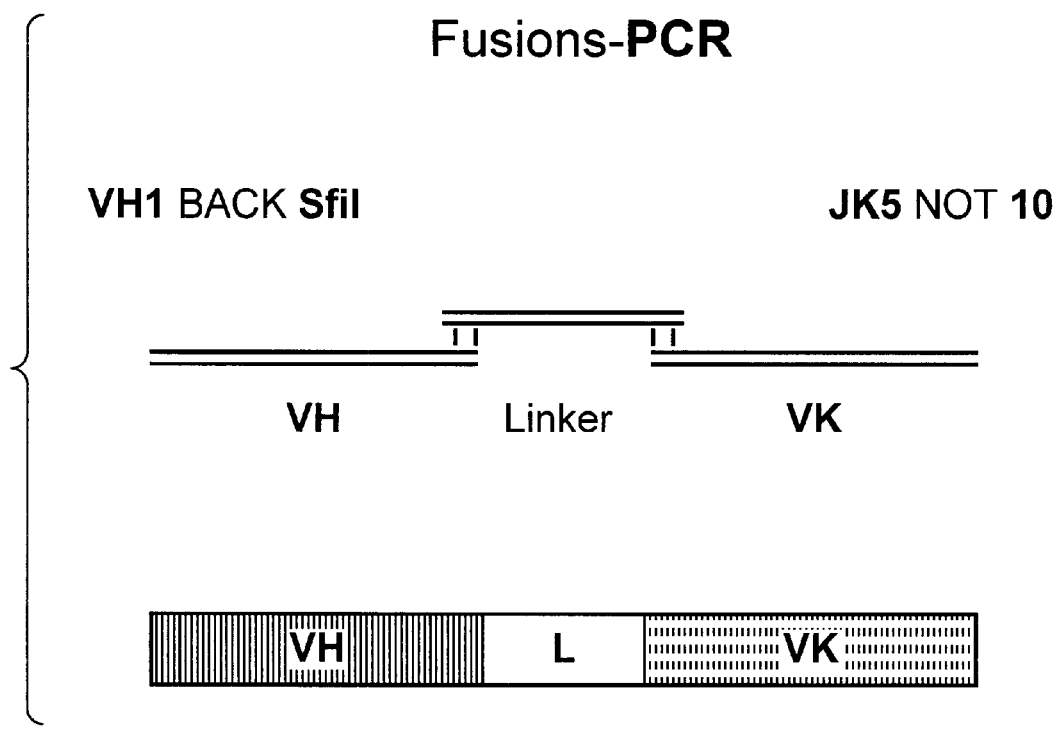
FIG. 3: Schematic representation of the construction of the scFv-ox (V-gene for V (variable) region, L linker).

To begin with, mRNA was isolated from the hybridoma cells and circumscribed into cDNA. This cDNA served as a matrix for the amplification of the variable immunoglobulins VH and VK with the specific primers VH1 BACK and BH FOR-2 for the heavy chain as well as VK2 BACK and MJK5 FON X for the light chain (Clackson et al., 1991 Nature 352, pgs. 624–628). The isolated variable immunoglobulin genes were the starting point for the construction of a single-chain antibody fragment (scFv). During the following fusion PCR, three components, VH, VK and a linker fragment, were united into a PCR reaction batch and the scFv-ox was amplified (FIG. 3). The so-constructed scFv-ox gene had a size of 735 bp. The variable domains were fused together in the sequence VH-L-VL.

Figure 4:
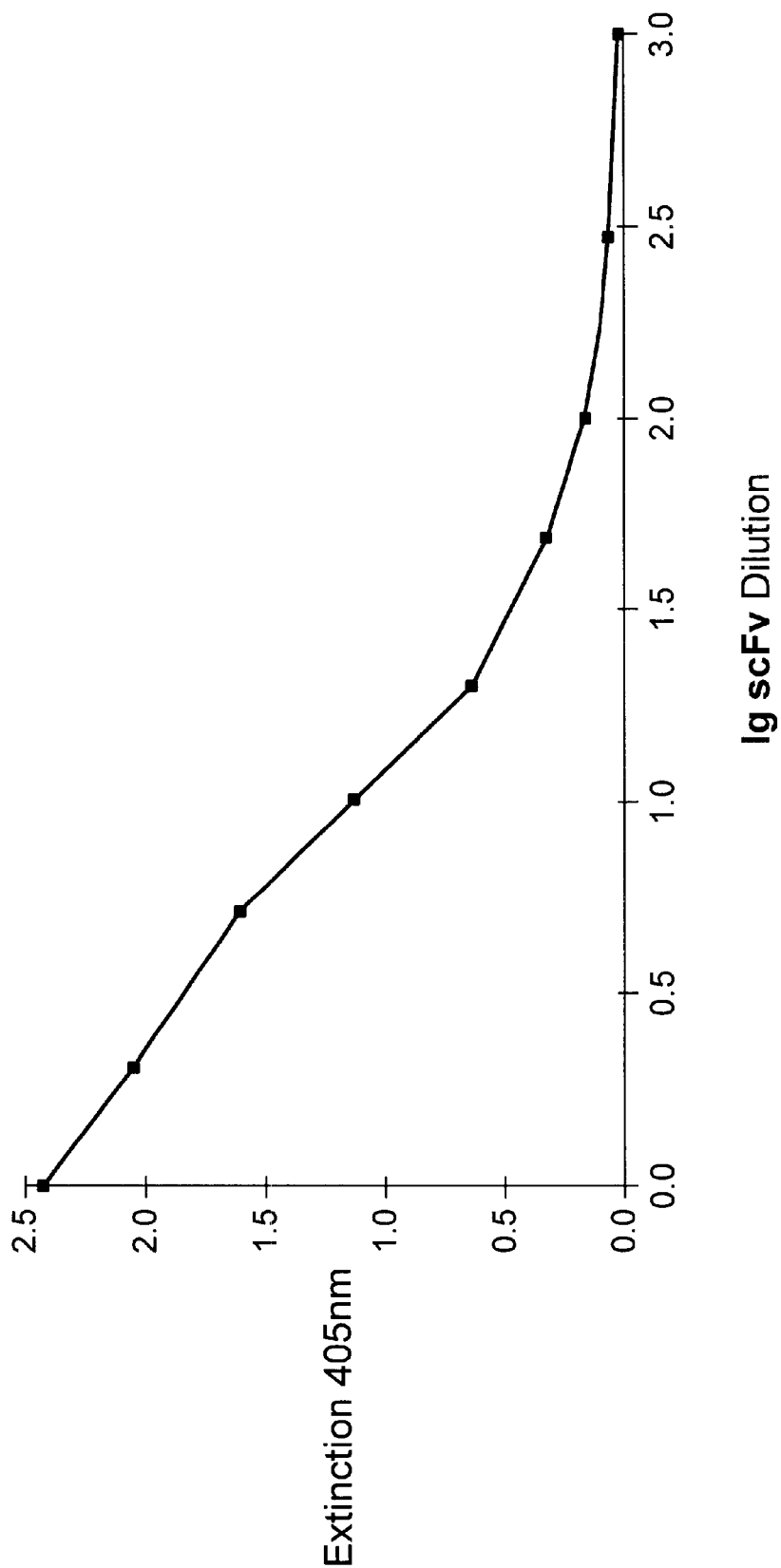
FIG. 4: Functional characterization of the scFv-ox 9 in the direct ELISA.

The functional characterization (antigen-binding activity) of the scFv-ox gene constructed took place after expression into a bacterial system. The scFv-ox was synthesized for this purpose as a soluble antibody fragment (Hoogenboom et al., 1991 Nature 352, pgs. 624–628). The activity and specificity of the antibody fragment constructed was checked in ELISA tests (FIG. 4).

Figure 5:
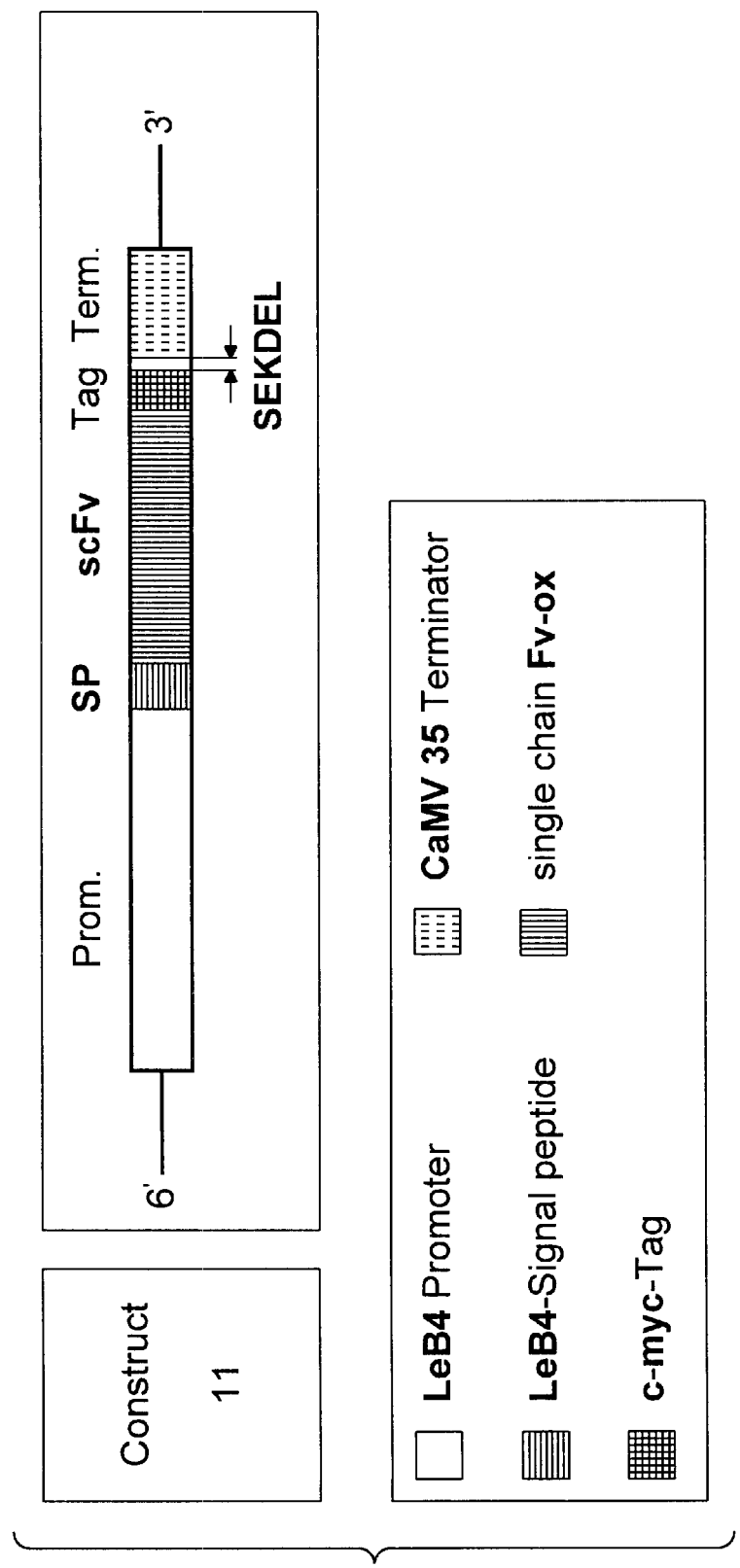
FIG. 5: Schematic representation of the cassette for the seed-specific expression of the scFv-ox gene.

In order to make possible a seed-specific expression of the antibody fragment in tobacco, the scFv gene was cloned downstream from the LeB4 promoter. The LeB4 promoter isolated from *Vicia faba* shows a strong seed-specific expression of various foreign genes in tobacco (Bäumlein et al., 1991, Mol. Gen. Genet. 225, pgs. 121–128; 1992, Plant J. 2, pgs.233–239). By transporting the scFv protein into the endoplasmic reticulum, a stable accumulation of high antibody fragment quantities was achieved. The scFv gene was fused for this purpose with a signal peptide sequence which the entry into the endoplasmic reticulum and the ER retention signal SEKDEL, which assured that it would remain in the ER (Wandelt et al., 1992Plant J. 2, pgs. 181–192) (FIG. 5).

The constructed expression cassette (construct 11) was cloned into the binary vector pGSGLUC1 (Saito et al., 1990 Plant Cell Rep. 8, pgs. 718,721) and transferred by electroporation into the Agrobacterium strain EHA 101. Recombinant agrobacterial clones were used for the subsequent transformation of *Nicotiana tabacum*. Tobacco plants (70–140) were regenerated per construct. Of the regenerated transgenic tobacco plants, both mature seeds and seeds in various stages of development were harvested after self pollination. The soluble proteins were obtained from these seeds after extraction into an aqueous buffer system. The analysis of the transgenic plants of the series 11 shows that, as a result of the fusion of the scFv gene with the DNA sequence of the ER retention signal SEKDEL, a maximum accumulation of 1.9% scFv proteins could be reached in mature seeds (Table 1).

TABLE 1

Summarizing representation of the seed-specific construct used, the number of tested and transgenic plants, their average scFv protein expression in the mature seed, as well as the antigen-binding activity of the antibody fragments. The levels of expression were determined by Western Blot Analyses, the specific binding activities by means of direct ELISA.

| Construct | No. of regen-erated plants | No. of trans-genic plants | No. of scFv protein expressing plants | Average/ highest expression level (% of TSP) | Average specific activity (OD/µg scFv) |
|---|---|---|---|---|---|
| [11] LeB4 SP-scFv-tag-SEKDEL | 103 | 65 | 64 | 0.98/1.90 | 1.36 |

In addition to investigations of accumulation, the question should be pursued as to whether the antibody fragments stored in mature seeds still have their biological activity, that is, still specifically bind the corresponding antigen, oxazolone. The specific activity was determined in the extracts of the mature tobacco seeds with a direct ELISA. The values thus obtained, which are given in Table 1, clearly show that the protein extracts manufactured from dry tobacco seeds contain functionally active antibody fragments. In further experiments, the stability of the antibody fragments accumulated in mature seeds after storage was investigated. For this purpose, the tobacco seeds were stored about one year at room temperature. The investigations showed that the amount and the activity of the accumulated antibody fragments are retained, even after storage for one-year.

Plant growth and seed development and production were not affected by synthesis of the recombinant proteins.

EXAMPLE 2

Seed-specific expression and accumulation of single-chain antibody fragments in the endoplasmic reticulum of cells of transgenic tobacco seeds controlled by the USP promoter.

The point of departure of the investigations was a single-chain antibody fragment against the phytohormone, abscisic acid (Artsaenko et al. 1994, J. Plant Physoil, 144, pgs. 427–429).

The functional characterization (antigen binding activity) of this constructed scFv-aABA gene was done after expression in a bacterial system and after expression in tobacco leaves (Artsaenko et al., 1994, J. Plant Physoil, 144, pgs. 427–429; 1995 Plant J 8, pgs. 745–750). The activity and the specificity of the constructed antibody fragment was checked in ELISA tests.

Figure 6:
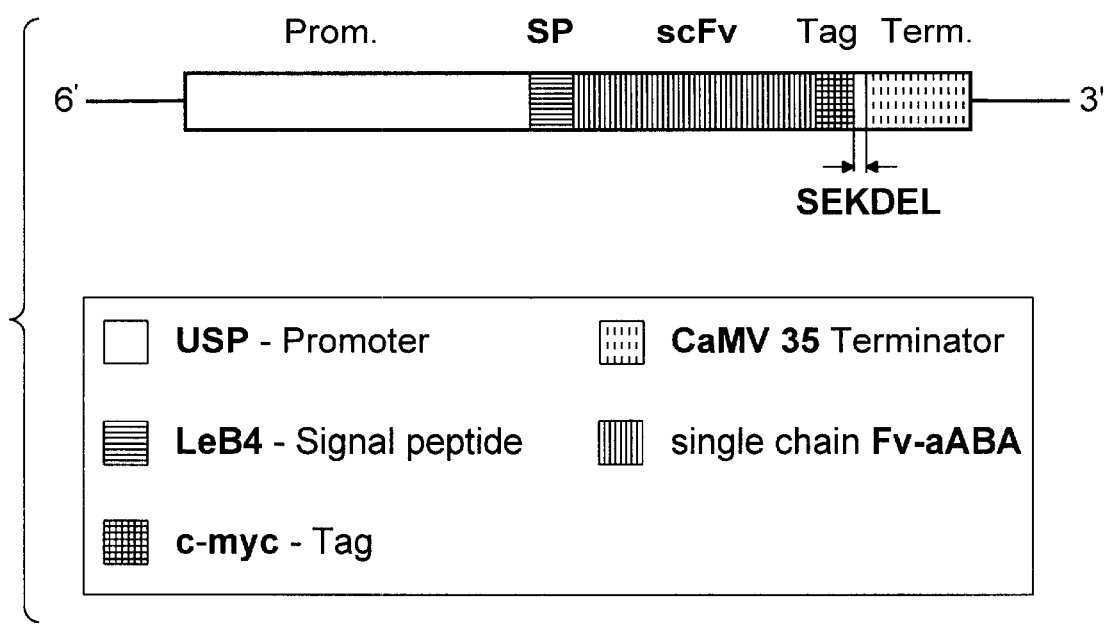
FIG. 6: Schematic representation of the cassette for seed-specific expression of the scFv-aABA.

In order to make possible a seed-specific expression of the antibody fragment in tobacco, the scFv gene was cloned upstream from the USP promoter. The USP promoter isolated from *Vicia faba* shows a strictly seed-specific expression of various foreign genes in tobacco (Fiedler et al., 1993, Plant Mol. Biol. 22, pgs. 669–679). By transporting the scFv protein into the endoplasmic reticulum, a stable accumulation of high antibody fragments was achieved. The scFv gene was fused for this purpose with a signal peptide sequence, which entry into the endoplasmic reticulum and the ER retention signal SEKDEL, which assures that it remains in the ER (Wandelt et al., 1992, Plant J. 2, pgs. 181–192) (FIG. 6).

The constructed expression cassette was cloned into the binary vector pGSGLUC1 (Saito et al., 1990, Plant Cell Rep. 8, pgs. 718–721) and transferred by electroporation into the Agrobacterium strain EHA 101. Recombinant agrobacterial clones were used for the subsequent transformation of *Nicotiana tabacum*. Both mature seeds and seeds in various stages of development were harvested from the regenerated transgenic tobacco plants after self-pollination. The soluble proteins were obtained from these seeds after extraction in an aqueous buffer system. The analysis of the transgenic plants shows that, as a result of the fusion of the scFv gene with the DNA sequence of the ER retention signal SEKDEL, under the control of the USP promoter, single-chain antibody fragments were synthesized beginning as early as day 10 of seed development.

The accumulation of the single-chain antibody fragments over the course of seed development was clearly stronger than in the case of expression controlled by the LeB4 promoter.

EXAMPLE 3

Expression of and stable accumulation of the single-chain antibody fragment scFv-ox in the leaf of transgenic tobacco plants and maintenance of the biological activity after harvesting and drying the leaf material.

The construction of the single-chain antibody fragment scFv-ox from the monoclonal antibody NQ 10-12.5 (Berek and Milstein, Immunol. Rev. 105, 5–26 (1988)) and its functional characterization after expression in the bacterial system, see Examples 1 and 2. In order to achieve a ubiquitous expression of the antibody fragment in the plant, especially in leaves, the scFv-ox gene was cloned upstream from the CaMV 35S promoter. This strong, virile constitutive promoter provides an expression of foreign genes in almost all plant tissue (Benfey and Chua, Science 250, 956–966 (1990)). By transporting the scFv protein into the endoplasmic reticulum, a stable accumulation of high antibody fragments was achieved in the leaf material. The scFv gene was first fused with the signal peptide sequence, which entry into the endoplasmic reticulum and the ER retention signal KDEL, which assures that it stays in the ER (Wandelt et al., Plant J. 2, 181–192 (1992)) (FIG. 1).

The constructed expression cassette (construct 9) was cloned into the binary vector pGSGLUC1 (Saito et al., Plant Cell Rep 8, 718–721 (1990)) and transferred by electroporation into the Agrobacterium strain EHA 101. Recombinant agrobacteria clones were used for the subsequent transformation of *Nicotiana tabacum*. Approximately 100 tobacco plants were regenerated. From the regenerated transgenic tobacco plants, leaf material was taken in various stages of development. The soluble proteins were obtained from this leaf material after extraction in an aqueous buffer system. Subsequent analyses (Western Blot Analyses and ELISA tests) showed that in leaves of series 9, a maximum accumulation of about 4% of biologically active antigen binding scFv protein could be obtained (Table 2). The high expression values were obtained in full-grown green leaves, but the antibody fragment could still be detected even in senescent leaf material.

TABLE 2

Summarizing representation of the construct used, which provides a ubiquitous expression of the scFv gene, the number of tested and transgenic plants, their average scFv protein expression in the leaf and the antigen-binding activity of the antibody fragments in the leaf extracts. The levels of expression were determined by Western Blot Analyses and the antigen binding activity by a direct ELISA.

| Construct | No. of regenerated plants | No. of transgenic plants | No. of scFv protein expressing plants | Average/ highest expression level (% of TSP) | Average specific activity (OD/µg scFv) |
| --- | --- | --- | --- | --- | --- |
| 9CaMV 35S SP scFv-tag-KDEL | 96 | 77 | 74 | 1.1/4.0 | 2.5 |

In the isolation of antibody fragments on a larger, even on an industrial scale, longer incubation times may be unavoidable. It is therefore necessary to test whether the scFv protein, after extraction from the respective tissue, is stable in the buffer system used. Extracts were produced from the leaves of plants expressing scFv fragments and incubated for 1 to 4 hours at room temperature without the addition of protease inhibitors. It was shown that, within the time period tested, there was no detectable decomposition of the antibody fragments in the extracts from leaves. The cause of the stability may be the compartment-specific occurrence of the antibody fragments, which leads to the fact that these antibody fragments, after homogenization of the tissue, do not occur together with the proteases in the soluble supernatant.

Figure 7:
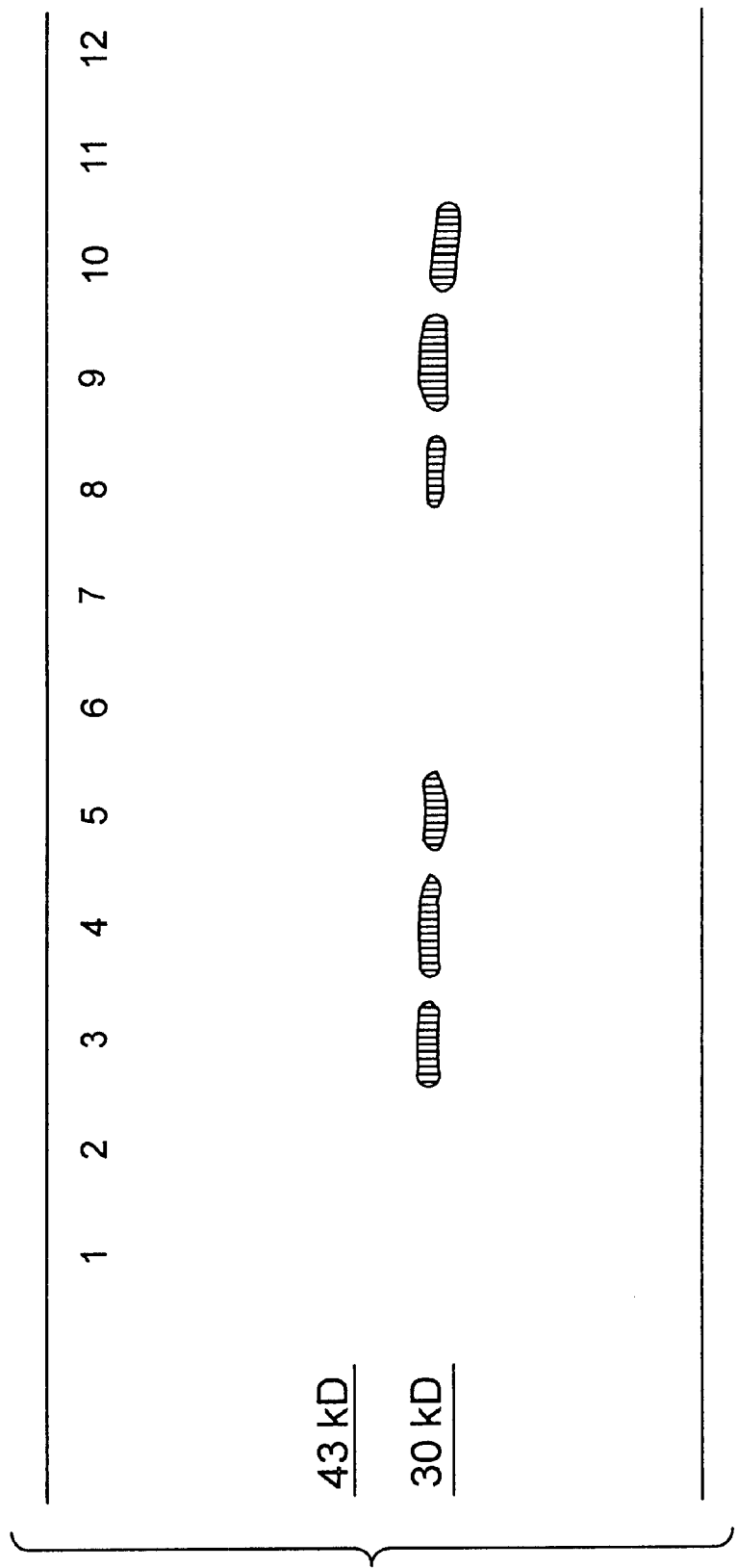
FIG. 7: Investigations of the stability of the scFv protein after drying the leaves of the transgenic plants 9/21 and 9/22 at room temperature and at 50° C. The scFv fragment was detected by Western Blot Analysis. 40 μg of total soluble protein was applied. Track 1: control plant SNN, Track 2: 100 ng of scFv protein, Track 3: 9/21 room temperature before drying, Track 4: 9/21 room temperature drying and 1 week storage. Track 5: 9/21 50° C. before drying. Track 6: 9/21 50° C. after drying. Track 7: 9/21 50° C. after drying and 3 weeks storage. Track 8: 9/22 room temperature before drying. Track 9: 9/22 room temperature drying and one week storage. Track 10: 9/22 50° C. before drying. Track 11: 9/22 50° C. after drying. Track 12: 9/22 50° C. after drying and 3 weeks storage. The sizes of the protein molecular weight standards are represented at the left.

In addition to the stability in the buffer system used for the extraction, the possibility of storage of the scFv protein plays an equally important role, since it is often impossible to process the harvested materials directly. In Example 1, it has already been described that, in the case of expression in the seed, storage for at least one year at room temperature can take place without measurable loss of accumulated antibodies or their activity. Storage of green tissue, while maintaining the amount and activity of antibodies is, however, not to be expected without reservations. Nevertheless, this was examined in a series of drying experiments. For this purpose, fully grown leaves of five plants of series 9 were harvested. A part of the leaf was immediately frozen (storage at −20° C.) and another dried at room temperature, and stored for one week under the same conditions. Parallel to this, leaves were dried at 50° C. and stored for three weeks at room temperature. The results of these investigations are shown in FIG. 7.

It was shown that the antibody fragments of the leaves dried at room temperature are still present even after storage for a week. Likewise the antigen-binding activity of the antibody fragment could be detected in a subsequent ELISA with extracts from the dried leaves. In this regard, no differences could be detected between the leaf material stored at −20° C. and the leaf material dried and stored at room temperature. In contrast to this, no scFv protein could be detected in leaves dried at 50° C. in the Western Blot Test (FIG. 7).

The plant growth was not affected by the production of the recombinant proteins.

EXAMPLE 4

Stable accumulation of the single-chain antibody fragment against the phytohormone abscisinic acid in the endoplasmic reticulum and the maintenance of biological activity after harvesting and drying of the leaf material of transgenic tobacco plants.

The starting point for the investigations was a single-chain antibody fragment expressed in tobacco plants against the phytohormone abscisinic acid (Artssenko et al., Plant J. 8, 745–750 (1995)). The quantity and activity of the synthesized scFv protein was determined in Western Blot Analyses and ELISA tests.

Figure 8B:
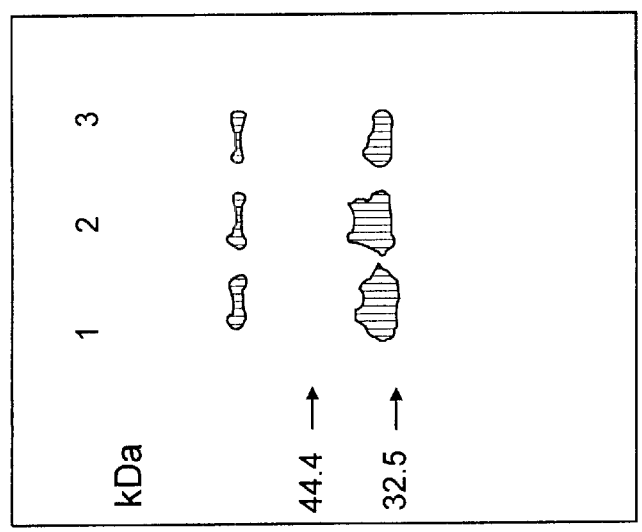
FIG. 8B: In each case, the quanities of scFv protein (about 100 ng), which were used for the ELISA analyses, is determined by Western Blot Analyses. The sizes of the protein molecular weight standards are represented at the left.
Figure 8A:
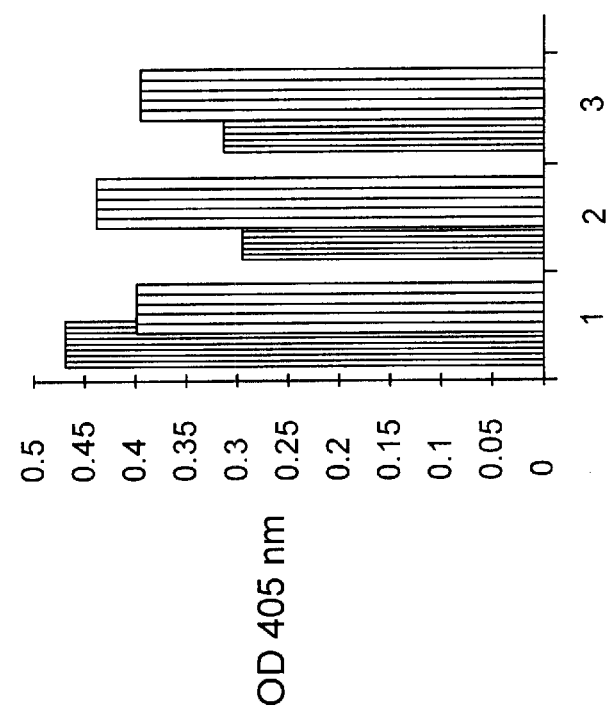
FIG. 8A: Evidence of maintenance of the antigen-binding activity of the antibody fragment scFv-ABA in leaves after drying or lyophilization, by means of ELISA tests.

In order to make possible the expression of the scFv in the endoplasmic reticulum, the foreign gene was expressed under the control of the CaMV 35S promoters as a translation fusion with the LeB4 signal peptide (N terminal) and the ER retention signal KDEL (C terminal). By transporting the scFv protein into the endoplasmic reticulum, a stable accumulation of a high amounts of active antibody fragments was achieved. After harvesting the leaf material, pieces of a leaf were frozen at −20° C., lyophilized or dried at room temperature. Soluble proteins were obtained from the leaf materials by extraction in an aqueous buffer, and the scFv protein purified by affinity chromatography. Identical quantities (FIG. 8B) of purified scFv protein (frozen, lyophilized and dried) were used to determine the activity of the antibody fragment (FIG. 8A). In this connection, approximately the same antigen-binding activities were detected.

What is claimed is:

1. A cassette for the seed-specific expression of storable proteins in tobacco plants, comprising:
    USP isolated from *Vicia faba* as a seed-specific promoter,
    DNA coding for the LeB4 signal peptide,
    a scFv gene for a single chain antibody fragment, for expression by said cassette, and
    DNA coding for ER retention signal, wherein the KDEL (SEQ. ID NO.: 1) amino acid sequence is used as ER retention signal.

2. The cassette of claim 1, wherein KDEL is further used to enhance the function of the USP promoter.

3. A cassette for the seed-specific expression of storable proteins in tobacco plants, comprising:
    LeB4 isolated from *Vicia faba* as a seed-specific promoter,
    DNA coding for the LeB4 signal peptide,
    a scFv gene for a single chain antibody fragment, for expression by said cassette, and
    DNA coding for ER retention signal, wherein the KDEL (SEQ. ID NO.: 1) amino acid sequence is used as ER retention signal.

4. The cassette of claim 3, wherein KDEL is further used to enhance the function of the LeB4 promoter.

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
       (A) LENGTH: 4 amino acids
       (B) TYPE: amino acid
       (C) STRANDEDNESS: single
       (D) TOPOLOGY: linear (ii) MOLECULE TYPE: peptide (x) PUBLICATION INFORMATION:
       (H) DOCUMENT NUMBER: WO 97/29200 A1
       (I) FILING DATE: 07-FEB-1997
       (J) PUBLICATION DATE: 14-AUG-1997

(xi) SEQUENCE DESCRIPTION: SEQ ID NO: 1:

Lys Asp Glu Leu
1

(2) INFORMATION FOR SEQ ID NO: 2:

(i) SEQUENCE CHARACTERISTICS:
       (A) LENGTH: 6 amino acids
       (B) TYPE: amino acid
       (C) STRANDEDNESS: single
       (D) TOPOLOGY: linear (ii) MOLECULE TYPE: peptide (x) PUBLICATION INFORMATION:
       (H) DOCUMENT NUMBER: WO 97/29200 A1
       (I) FILING DATE: 07-FEB-1997
       (J) PUBLICATION DATE: 14-AUG-1997

-continued (xi) SEQUENCE DESCRIPTION: SEQ ID NO: 2:

```
Ser Glu Lys Asp Glu Leu
1               5
```